United States Patent [19]

Barberet-Maiolino et al.

[11] Patent Number: Plant 7,242

[45] Date of Patent: Jun. 5, 1990

[54] SPRAY CARNATION NAMED LONGPOL

[75] Inventors: Nicole Barberet-Maiolino; Henri Blanc, both of Antibes, France

[73] Assignee: Laboratoire de Physiologie Vegetale, La Londe-Les-Maures, France

[21] Appl. No.: 255,440

[22] Filed: Oct. 11, 1988

[51] Int. Cl.[5] ..... A01H 5/00

[52] U.S. Cl. ..... Plt./70

[58] Field of Search ..... Plt./70

*Primary Examiner*—James R. Feyrer

*Attorney, Agent, or Firm*—Charles W. Rummler

[57] ABSTRACT

A new and believed to be original spray carnation variety particularly distinguished by the very unusual coloration of purple-violet to white for its small to medium sized blossoms, which are produced intermittently and profusely during the Spring, Summer and Fall blooming periods; the plant itself having a vigorous, upright and rigid growth habit with very abundant foliage reaching a height of about 99 cm. during eight months of growth.

1 Drawing Sheet

BACKGROUND OF THE NEW PLANT

This new spray carnation cultivar originated as a seedling of a hybrid developed by us in 1983 at our nursery at 83250 La Londe-Les-Maures, France, by crossing two varieties selected from our collection of breeding plants maintained at our nursery for breeding purposes. This particular seedling was selected for propagation because of its very unusual flower coloration and the overall high quality of the plant growth on which the blooms were produced and asexual propagation of this selected plant was done by us and under our direction at La Londe with such satisfactory results that we directed that propagation of this new plant be continued from generation to generation both by cuttings and by in vitro propagation procedures to determine whether the novel characteristics of the selected plant would be retained from generation to generation and its homogeneity could be assured. This proved to be successful and this new spray carnation variety is now being propagated on a commercial scale at La Londe.

DESCRIPTION OF THE DRAWING

Our new spray carnation cultivar is illustrated by the accompanying photographic drawing, which shows a blooming portion of a spray stem with buds and flowers in several stages of development, the color rendition being as nearly true as is reasonably possible to obtain by professional photographic procedures.

DESCRIPTION OF THE NEW PLANT

The following is a detailed description of our new spray carnation variety based upon observation of plants grown in greenhouse as well as outdoors at La Londe and blooming during the current year. The color designations stated herein are according to The R.H.S. Colour Chart published by The Royal Horticultural Society of London, England.

THE PLANT

Origin: Seedling.

Parentage:

*Seed parent.*—Variety No. 82 MG 7 (unpatented).

*Pollen parent.*—Variety No. 79 MFB 5 (unpatented). Both varieties are identified in our breeding records maintained at our nursery at La Londe.

Classification:

*Botanic.*—*Dianthus caryophyllus.*

*Commercial.*—Spray Carnation.

Form: Erect bush having at least four stems emitted near the ground.

Height: In average, about 99 cm. at eight months of growth.

Main stem length: Less than 15 cm. due to pinching.

Growth: Vigorous, upright and rigid.

Branching character: Average.

Foliage:

*Quantity.*—Very abundant.

*Number of leaves.*—More than 120.

*Leaf size.*—About 12.9 cm. long and 0.6 cm wide at the seventh node.

*Leaf shape.*—Oblong with curved margins.

*Texture.*—Leathery.

*Ribs and veins.*—Hardly noticeable.

*Rachis.*—Hardly noticeable.

*Color.*—Both upper side and under side, between 189-A and 189-B.

*Leaflets.*—None.

THE BUD

Size: Small.

*Diameter.*—Averaging about 1.4 cm.

*Length.*—Averaging about 2.7 cm.

Shape: Long cylindrical.

Rate of opening: Normal.

Color of petals: When sepals first divide, 78-B to 155-D. When petals begin to unfurl, 80-B/78-B to 155-D.

Sepals:

*Number.*—Five or six.

*Shape.*—Generally ovate but joined together at the lower parts and having an acuminate apex.

*Character.*—The sepals are hooded over the bud and stand up when the flowers open.

*Color.*—Inside, 145-D. Outside, 137-C and 145-A.

*Striae.*—Longitudinal.

Calyx:

*Shape.*—Cylindrical and long.

*Splitting.*—The calyx does not split.

*Aspect.*—Smooth

Flower stem:

*Character.*—Erect and rigid.
*Color.*—189-A/189-B.

THE FLOWER

Blooming habit: Recurrent, blooming profusely in the Spring, midseason and Fall blooming periods with a tendency to give few blooms in Fall.
Size of flower: Small.
*Diameter.*—Averaging about 6 cm.
*Depth.*—Averaging about 5.5 cm.
Borne: Singly on an individual stem of a cluster.
Shape: When bloom first opens, high centered. When bloom matures, dome-shaped.
Petalage:
*Number of petals.*—In average, about thirty-six.
*Arrangement.*—Imbricated.
*Form.*—Fan-shaped with rounded edges and a round apex.
*Texture.*—Leathery.
*Aspect.*—Satiny.
*Color.*—Both outer petals and inside petals: Body — Shaded with Purple Violet and Imperial Purple 80-B/78-B to White 155-D. Base — Greenish. Reverse side — 78-B to 155-D.
Petaloids:
*Number.*—Less than six.
*Size.*—Smaller than the petals.
*Color.*—The same as the petals.
Flower stem:
*Length.*—Averaging about 58.8 cm. cut at the tenth node.
*Character.*—Upright with good strength.
*Color.*—189-A/189-B.

Fragrance: Strong.
Discoloration after full bloom: Very little.
Persistence: The flowers hang on and dry.
Disease resistance: Resistant to *Fusarium oxysporum* as observed I.N.R.A. 06600 Antibes, France.
Lasting quality: At least ten days as a cut flower in vase keeping.

REPRODUCTIVE ORGANS

Stamens:
*Number.*—Four to twelve.
*Arrangement.*—Encircling the ovary.
*Anthers.*—Size: About 4 mm. Color: Violet.
*Filaments.*—Length: About 3 cm., in average. Color: Whitish.
Pistils:
*Number.*—Two to four.
*Styles.*—Length: Averaging about 3 cm. Color: Whitish.
*Stigma.*—Color: Whitish.
Character of ovaries: Ribbed.

This plant is believed to be an original variety. However, its characteristics may be somewhat modulated under various conditions of environment and where and when the plant is grown.

We claim:

1. The new and distinctive carnation plant, substantially as herein shown and described, particularly characterized by the purple to white coloration of its flowers and the profuse production of flowers on strong, upright stems having abundant foliage.

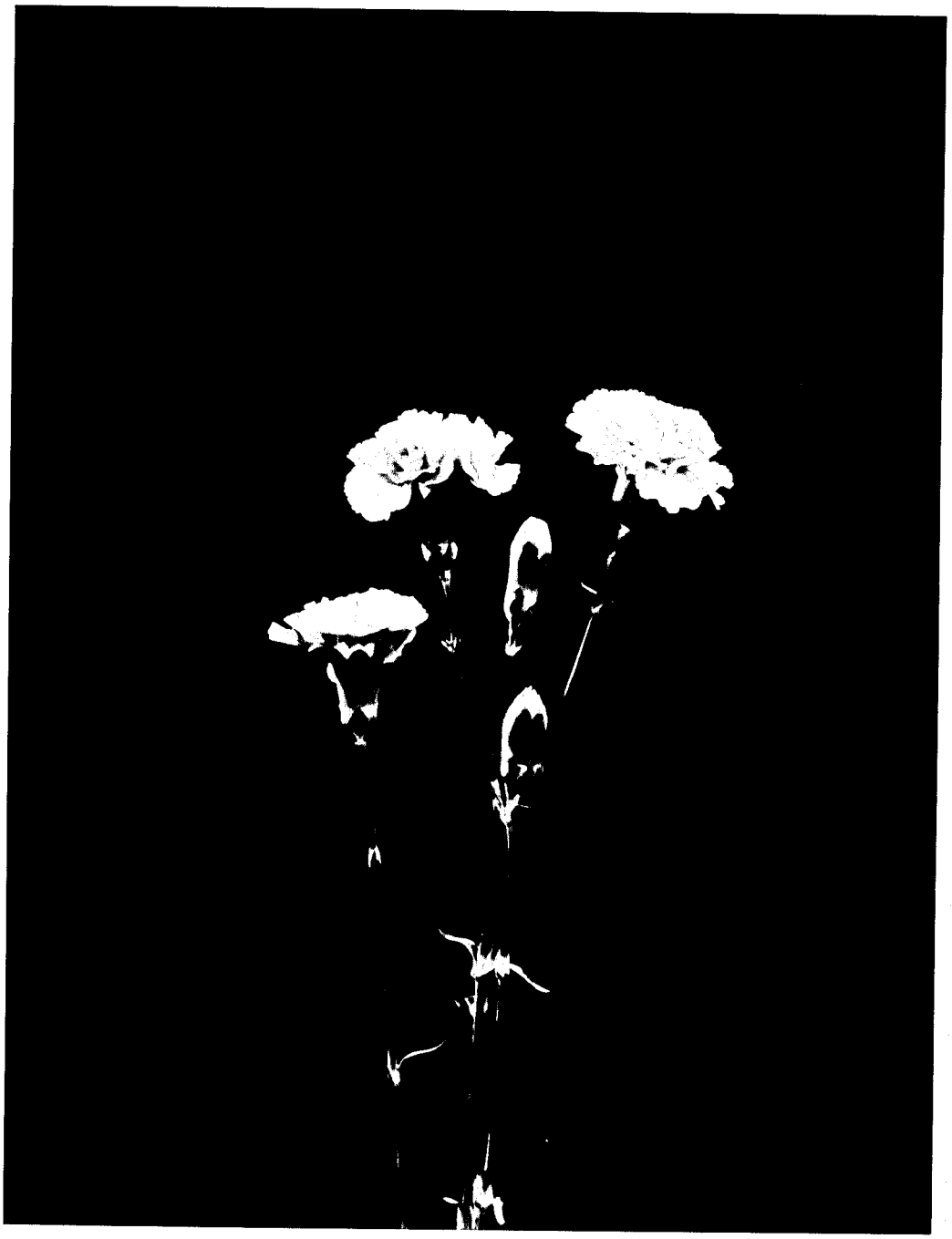

* * * * *